(12) United States Patent
Kipper et al.

(10) Patent No.: US 7,858,093 B1
(45) Date of Patent: Dec. 28, 2010

(54) CONTROLLED-RELEASE IMMUNOGENIC FORMULATIONS TO MODULATE IMMUNE RESPONSE

(75) Inventors: Matthew J. Kipper, Gaithersburg, MD (US); Balaji Narasimhan, Ames, IA (US); Jennifer H. Wilson, Ames, IA (US); Michael J. Wannemuehler, Gilbert, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 11/262,310

(22) Filed: Oct. 28, 2005

Related U.S. Application Data

(60) Provisional application No. 60/623,711, filed on Oct. 29, 2004.

(51) Int. Cl.
*A61K 39/00* (2006.01)
*A61K 49/00* (2006.01)
*A61K 39/02* (2006.01)

(52) U.S. Cl. ............ 424/184.1; 424/9.1; 424/9.2; 424/200.1; 424/204.1; 424/234.1; 424/278.1; 424/280.1; 424/93.1

(58) Field of Classification Search ............ 424/9.1, 424/9.2, 184.1, 200.1, 204.1, 234.1, 278.1, 424/280.1, 93.1
See application file for complete search history.

(56) References Cited

U.S. PATENT DOCUMENTS 4,990,336 A * 2/1991 Silvestri et al. ............ 424/426

2010/0021546 A1  1/2010  Kipper et al.

OTHER PUBLICATIONS

Gallo, R.C., "The end or the beginning of the drive to an HIV-preventive vaccine: a view from over 20 years", Lancet, vol. 366, pp. 1894-1898, 2005.*
Wang, J., et al, "Tuberculosis vaccines: the past, present and future", Expert Rev. Vaccines, vol. 1, No. 3, pp. 341-354, 2002.*
Shen, E., et al. Mechanistic relationships between polymer microstructures and drug release kinetics in bioerodible polyanhydrides. Journal of Controlled Release, vol. 82, pp. 115-125, 2002.*
Kipper, M.J., et al. Design of an injectable system based on bioerodible polyanhydride microspheres for sustained drug delivery. Biomaterials, vol. 23, pp. 4405-4412, 2002.*
Kipper, M. J., et al., "Polymeric Biomaterials with Tailored Microstructures, Nanostructures, and Bioactive Surface Chemistries for Drug Delivery and Tissue Engineering", *Conference Proceedings, Annual Meeting of the American Institute of Chemical Engineers*, obtained from http://aiche.confex.com/aiche/2005/techprogram/P9686.HTM,(Oct. 2005),4 p.
Kipper, M. J., et al., "Single Dose Tetanus Vaccine Based on Polyanhydride Microspheres", *Conference Proceedings, Annual Meeting of the American Institute of Chemical Engineers*, Abstract No. 68a, obtained from http://www.aiche.org/conferences/techprogram/paperdetail.asp?PaperID=2163&DSN=annual04,(Oct. 2005),2 p.
Determan, A. S., et al., "Encapsulation, Stabilization, and Release of BSA-FITC From Polyanhydride Microspheres", *Journal of Controlled Release, 100*, (2004),97-109.

* cited by examiner

*Primary Examiner*—Rodney P. Swartz
(74) *Attorney, Agent, or Firm*—Schwegman, Lundberg & Woessner, P.A.

(57) ABSTRACT

Single-dose controlled-release immunogenic formulations, such as vaccines, based on bioerodible polyanhydride copolymer or homopolymer microparticles for the control of immune response mechanisms are provided. The copolymer or homopolymer microparticles degrade by surface-erosion from in vivo hydrolysis of anhydride linkages at the surface of the microparticle, which results in controlled release of immunogen(s) to a patient.

30 Claims, 7 Drawing Sheets

CONTROLLED-RELEASE IMMUNOGENIC FORMULATIONS TO MODULATE IMMUNE RESPONSE

CROSS-REFERENCE TO RELATED APPLICATIONS

This patent application claims the benefit of priority, under 35 U.S.C. Section 119(e), to U.S. Provisional Patent Application Ser. No. 60/623,711, filed on Oct. 29, 2004, which is incorporated herein by reference.

BACKGROUND OF THE INVENTION

While the development of effective single dose vaccines would have major implications for the effectiveness of mass immunization programs, the development of single dose vaccines is fraught with a complex combination of clinical and engineering challenges. Several health organizations have listed the development of single dose vaccines as one of the "grand challenges" of human health worldwide. Even diseases for which effective vaccines exist remain a threat to public health because patient dropout rates (after initial vaccinations) reach as high as 70% in developing countries (Aguado, M. T.; Lambert, P.-H. (1992) *Immunobiology* 184, 113-125.). Improved vaccine delivery techniques that require only a single dose to confer protective immunity against childhood diseases would help make mass immunization programs successful. For instance, tetanus is responsible for over 700,000 neonatal deaths annually, half of which could be prevented by immunization alone.

Induction of the appropriate immune response is essential to the safety and efficacy of vaccines (Woodland, D. L. (2004) *Trends Immunol.* 25, 98-104). While traditional alum-based vaccines, incorporating tetanus toxoid (TT) in particular, initiate primarily a T helper type 2 ($T_H2$) response (Singh, M.; O'Hagan, D. T. (2003) *Int. J. Parasitology* 33, 469-478), a T helper type 1 ($T_H1$) response may be more effective for protection from or treatment of cancers or infections due to intracellular pathogens (Hanes, J., Cleland, J. L., Langer, R. (1997) *Adv. Drug Del. Rev.* 28, 97-119). However, the mechanisms governing the type of immune response are complex and not completely understood (Sedlik, C., Dériaud, E., Leclerc, C. (1997) *Int. Immunol.* 9, 91-103). The $T_H2$ (humoral) response, characterized by the activation of B cells that differentiate into plasma cells that secrete antibodies, is effective to neutralize extracellular pathogens and toxins, but not to neutralize intracellular pathogens. The $T_H1$ (cell-mediated) response, involving the activation of interferon-γ producing $CD4^+$ T cells, $CD8^+$ cytotoxic ("killer") T cells, and macrophages, is effective against intracellular pathogens (Finkelman, F. D.; Urban, J. F. J. (1992) *Parasitol. Today* 8, 311-314). The ability to purposefully modulate the immune response to more effectively protect the host from a particular pathogen would improve the effectiveness of vaccines in combating many worldwide diseases.

A single-dose vaccine would alleviate problems associated with conventional vaccination programs that have high dropout rates. Also, no currently existing formulation can provide a tunable immune response in a single-dose formulation. Accordingly, there is a need for development of improved technologies or regimen that allow for the development of new single-dose vaccines for intracellular pathogens that require a preferential induction of the $T_H1$ immune response. A need also exists for development of improved technologies or regimen that allow for the development of new single-dose vaccines that induce a balance of both the $T_H1$ and $T_H2$ responses for protection from other conditions such as HIV/AIDS and certain types of cancers.

SUMMARY OF THE INVENTION

The present invention provides a single dose immunogenic composition, such as a vaccine, based on biodegradable polymer microparticles. The single dose immunogenic composition, such as a vaccine, contains an effective amount of an immunogen incorporated into a bioerodible polyanhydride copolymer or homopolymer microparticle, such as a microsphere. The microparticles can stabilize proteins and target their delivery to dendritic cells so that the vaccine results in immunity after administration of only a single-dose, by prolonging exposure to the immunogen. The immune response mechanisms ($T_H1$ vs. $T_H2$) can be adjusted or "tuned" by altering the composition of the polyanhydride(s) and of the immunogen(s) in the immunogenic composition, such as a vaccine, formulation.

The invention provides a single dose immunogenic composition, such as a vaccine, comprising an effective amount of an immunogen incorporated into bioerodible polyanhydride copolymer or homopolymer microparticles so that an amount of immunogen effective to immunize an animal against a pathogen is provided to said animal following administration of a single dose of said microparticles. The invention also provides sustained exposure to an immunogen that can result in maintenance of immuno-regulatory mechanisms. Such therapies could include treatments for autoimmune diseases (e.g. diabetes), allergic reactions, or immune mediated inflammatory diseases (e.g. colitis). The animal can be a human, a domesticated animal such as a companion animal or a farm animal. The immunogenic composition, such as a vaccine, can induce both a primary and secondary immune response in the subject. The immunogenic composition, such as a vaccine, can be derived from any pathogen that elicits a $T_H1$ or $T_H2$ response in an animal. The immunogenic composition, such as a vaccine, can induce a balanced immune response, wherein the $T_H1$ and $T_H2$ responses are substantially equivalent, in that they both arise and make an effective contribution to immunity.

The immunogenic composition, such as a vaccine, includes a carrier particle having a polyanhydride matrix, wherein the polyanhydride is a homopolymer or a copolymer of a 1,ω-bis(p-carboxyphenoxy)($C_2$-$C_{12}$)alkane, preferably a ($C_4$-$C_8$)alkane with a ($C_5$-$C_{20}$)alkanoic diacid, preferably a ($C_8$-$C_{12}$)alkanoic diacid. The ($C_5$-$C_{20}$)alkanoic diacid can be sebacic acid (SA). The 1,ω-bis(p-carboxyphenoxy) ($C_1$-$C_6$) alkane can be 1,6-bis(p-carboxyphenoxy)hexane (CPH). The molar ratio of CPH:SA can be less than about 1:1, preferably about 1:1.5-5. The microparticles can be about 100 nm to about 100 μm in diameter, about 100 nm to about 75 μm, or more specifically about 100 nm to about 50 μm in diameter.

In addition to entrapped immunogen, the immunogenic composition, such as a vaccine, also preferably includes an amount of free immunogen effective to provide a balanced immune response in said animal. Thus, the immunogenic composition, such as a vaccine, can elicit a $T_H1$ immune response in conjunction with a $T_H2$ immune response. The immunogenic composition, such as a vaccine, can stimulate the production of interleukin 12 (IL-12). The immunogenic composition, such as a vaccine, can stimulate $T_H1$ cells that produce interferon γ (INF-γ) in sufficient quantity to suppress IgG1 production.

A method is provided to induce an immunogenic response in an animal comprising administering to said animal an effective immunogenic amount of the immunogenic composition, such as a vaccine, of the invention, preferably in combination with an aqueous liquid vehicle. The immunogenic composition, such as a vaccine, can be administered by injection or intranasal spray. The immunogenic composition, such as a vaccine, can reduce at least one of the symptoms of infection by a pathogen. The immunogenic composition, such as a vaccine, can be used to vaccinate against a pathogen such as a gram-positive bacterium or *bacillus*. For example, the pathogen can be *C. tetani, C. botulinum, B. anthracis,* or *C. diphtheriae*. The pathogen can also be an acid-fast bacterium such as *M. tuberculosis* or *M. bovis*. The vaccine can be used to vaccinate against a pathogen such as a gram-negative bacterium. For example, the bacterium can be a shigellae, salmonellae, bordetellae, francisellae, or yersiniae. The pathogen can also be a spirochete, a chlamydiae, a staphylococci, a streptococci, a pneumococci, or a neisseriae. The pathogen can be a parasite or portion derived from a parasite such as *Leishmania, Toxoplasma, Plasmodium* (malaria), trypanosomes or *Giardia* species. The pathogen can be a virus, such as HSV, HIV, EBV, a poliovirus, an influenza virus, a rabies virus, a variola virus, a yellow fever virus or a hepatitis virus. The virus can be a retrovirus, and the retrovirus can be HIV. The pathogen can also be yeast or fungal in nature, including *Hitsoplasma, Cryptococcus,* or *Coccidioides* species.

The immunogen can include a polypeptide or polypeptide subunit of one or more of the pathogens recited herein. The immunogen can be an inactivated polioviruses, rabies virus, vaccinia virus, or yellow fever virus. The immunogen can be a polypeptide or polypeptide subunit of a bacilli, a cocci or other bacterial morphologies. The bacilli can be typhoid, pertussis, or plague. The immunogen can include a polypeptide or polypeptide subunit of a spirochete. The immunogen can include diphtheria toxoids or tetanus toxoids. The immunogen can also include a polypeptide, or polypeptide subunit of a parasite or a virus. The immunogen can also be an oligosaccharide, an oligonucleotide (e.g. DNA), or an allergen.

The development of a single-dose tetanus toxoid (TT) immunogenic composition, such as a vaccine, based on polyanhydride microspheres composed of 1,6-bis(p-carboxyphenoxy)hexane (CPH) and sebacic acid (SA) is disclosed hereinbelow. Release kinetics can be modulated by altering the copolymer composition, which allows various immunization regimens to be developed. In vivo studies in mice demonstrated that the encapsulation procedure preserves the immunogenicity of TT. The polymer itself can have an adjuvant effect, enhancing the immune response to a small dose of TT, but as the dose of polymer is increased, a localized, dose-dependent inhibition of the immune response may be observed.

Sustained release of antigenic/immunogenic protein is essential for the efficacy of a single-dose vaccine. TT released from the microspheres maintained its immunogenicity and antigenicity and the microspheres provided a prolonged exposure to TT sufficient to induce the secondary immune response (i.e., isotype switching, high avidity, and high titers were observed) without requiring an additional administration. In addition to providing an immune response with a single immunizing dose, the microsphere delivery vehicle offers the opportunity to select the preferred immune response pathway. While TT administered in buffer alone is known to induce a dominant $T_H2$ immune response, the TT-loaded microspheres described herein can induce a balanced $T_H1$ and $T_H2$ immune response pathways as evidenced by the observed IgG2a and IgG1 antibody responses, respectively, when they are injected intramuscularly.

DETAILED DESCRIPTION OF THE INVENTION

Figure 1A:
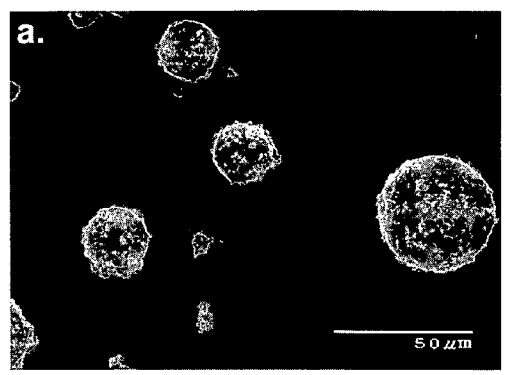
FIG. 1a and FIG. 1b illustrate scanning electron micrographs of TT-Loaded 20:80 poly(CPH-SA) microspheres.

The invention provides a single dose immunogenic composition, such as a vaccine, comprising biodegradable polymer microparticles containing an effective amount of at least one immunogen. In one embodiment, the invention comprises microspheres based on polyanhydride homopolymers and copolymers of 1,ω-bis(p-carboxyphenoxy)alkanes and 1,ω-dicarboxylic alkanes such as 1,6-bis(p-carboxyphenoxy) hexane and sebacic acid, loaded with an antigenic protein that has the ability to provide immunity to a subject following administration of a single dose. For example, an effective dose of tetanus toxoid (TT) can be entrapped in the present bioerodible polyanhydride microspheres. As used herein, "entrapped" refers to the incorporation or partial incorporation of an immunogen into and/or onto the matrix of a polyanhydride microparticle.

Polyanhydrides provide a hydrophobic environment that can stabilize the immunogen until it is released. Useful polymer formulations include those which have hydrophobic and hydrophilic domains, such as anhydride copolymers. Such polymers are disclosed in, e.g., U.S. Pat. Nos. 4,757,128; 4,857,311; 4,891,225; 4,906,474; 5,019,379; 5,019,379; 5,543,158; 5,629,009; 5,718,921; 5,922,357; and 6,753,015.

Suitable polymer matrices also include homopolymers or copolymers formed from of monomers such as alkane bis-carboxylic acids and 1,ω-bis(carboxyaryloxy)alkanes. The alkane bis-carboxylic acid can be, for example, sebacic acid, or a corresponding anhydride such as sebacic anhydride. The 1,ω-bis(carboxyaryloxy)alkane can be, for example, 1,6-bis (p-carboxyphenoxy)hexane. The in vitro release kinetics can be modulated by altering the copolymer composition. The in vitro release profiles indicate that the formulations investigated can provide a sustained exposure of the vaccinated subject to the antigen, obviating the requirement of multiple injections to obtain protective immunity.

The microspheres are capable of targeted delivery to dendritic cells (DCs) when delivered by intramuscular, subcutaneous, or intradermal injection suspended in a vehicle such as saline with a small amount of dispersant (i.e., surfactant), such as fetal calf serum. This strategy results in preferential induction of a balanced T helper type 1 ($T_H1$) and T helper type 2 ($T_H2$) immune response (i.e., $T_H0$), as opposed to the dominant T helper type 2 ($T_H2$) immune response, typical of alum-based vaccine formulations and tetanus toxoid formulations in particular. Additionally, the $T_H1$ immune response can be enhanced by addition of free antigen to the microparticle suspension.

Bioerodible polymers are used to entrap immunogens for delivery to a patient. The properties of the polymers can be tailored by selecting various monomers that will have appropriate properties for encapsulation/entrapment and delivery of the immunogenic composition, such as a vaccine. The phase behavior of biodegradable polyanhydride blends is discussed by Kipper et al. ((2004) *Polymer,* 45(10), 3329-3340) and microphase separation in bioerodible polyanhydrides for drug delivery is described by Shen et al. ((2001) *Biomaterials,* 22, 201-210) and Kipper et al. ((2005) *Macromolecules,* 38, 8468-8472). The crystallinity of the homopolymers and copolymers is described by Kipper et al. ((2005) *J. Polym. Sci. Part B: Polym. Phys.,* 43, 463-477).

The surface-erodible polyanhydrides of the invention include poly(bis-(1,ω-carboxyphenoxy)($C_2$-$C_{12}$)alkane-co-($C_5$-$C_{20}$)bis-alkanoic acids). The substituents on the phenoxy moiety can be orientated ortho, meta, or para to each other, and are typically in a para relationship. The alkane moiety of the bis-(carboxyphenoxy) alkane can be a ($C_2$-$C_{12}$)alkane. Specifically, the alkane moiety can be a ($C_4$-$C_8$)alkane, and more specifically a ($C_6$)alkane. The alkanoic diacids used for the bioerodible polymers can be a ($C_5$-$C_{20}$)alkane bis-carboxylic acid. Specifically, the bis-carboxylic acid can be a ($C_6$-$C_{16}$)alkane bis-carboxylic acid, a ($C_8$-$C_{12}$)alkane bis-carboxylic acid, or more specifically a ($C_{10}$)alkane bis-carboxylic acid. The alkane and aryl moieties of the copolymers can optionally be substituted in a manner that increases or decreases hydrophobicity of the microparticles. The polymers can typically have the general formula 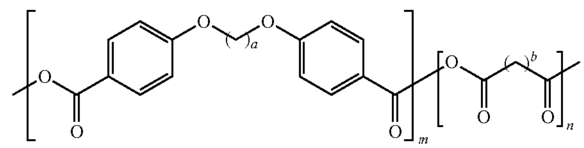 where m and n represent the number of repeating units of each monomer. The variables m and n are not less than one and are typically greater than ten. Alternatively, homopolymers may also be used, in which case either m or n would be zero. The variable a can be about 2-12 and the variable b can be about 5-20.

The copolymers are typically synthesized by melt polycondensation from acetylated prepolymers, for example, using the technique described by Kipper et al. ((2002) *Biomaterials* 23, 4405-4412)). Useful polyanhydrides can also be prepared by microwave polymerization as described by Vogel et al. ((2004) *Macromol. Rapid Comm.,* 25, 330-333). Other techniques known to those of skill in the art can also be used to prepare the copolymers. The polymers can have molecular weights of about 4,000 to about 55,000, specifically about 8,000 to about 30,000, and more specifically about 12,000 to about 22,000.

Any suitable and effective ratio of monomers can be used in the polyanhydride copolymers. The carboxyphenoxyalkane (CPA) to alkanoic diacid (AD) ratio can be about 1:1 to about 1:10. Certain embodiments of the invention employ ratios that are about 1:1, about 1:1.5, about 1:2, about 1:3, about 1:4, about 1:5, and about 1:9.

The polymer microparticles of the invention degrade by surface-erosion from in vivo hydrolysis of anhydride linkages at the surface of the microparticle, which results in controlled release of immunogen(s) to a patient. Surface-erodible biomaterials useful for the delivery of immunogens by the techniques disclosed herein are described by Narasimhan and Kipper ((2004) *Adv. Chem. Eng.,* 29, 169-218). Microstructural characterization of polyanhydride blends for controlled drug delivery are described by, for example, Shen et al. in *Biomaterials for Drug Delivery and Tissue Engineering,* Eds. Mallapragada, S. K., Tracy, M., Narasimhan, B., Mathiowitz, E. and Korsmeyer, R. (2001) *Mater. Res. Soc. Symp. Proc.* 662, NN4.2.1-4.2.5.

The erosion kinetics of and the drug release kinetics from polyanhydride homopolymers and copolymers composed of 1,6-bis(p-carboxyphenoxy) hexane (CPH) and sebacic acid (SA) has been reported (Shen, E., Kipper, M. J., Dziadul, B., Lim, M.-K., Narasimhan, B. (2002) *J. Controlled Release* 82, 115-125; Larobina, D., Kipper, M. J., Mensitieri, G., Narasimhan, B. (2002) *AIChE J.* 48, 2960-2970; Kipper, M.

J., Narasimhan, B. (2005) *Macromolecules* 38, 1989-1999). Polyanhydride CPH:SA copolymers can have the general formula:

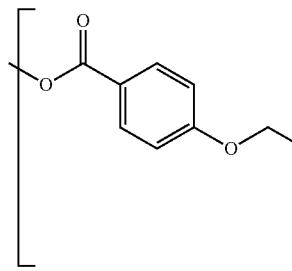 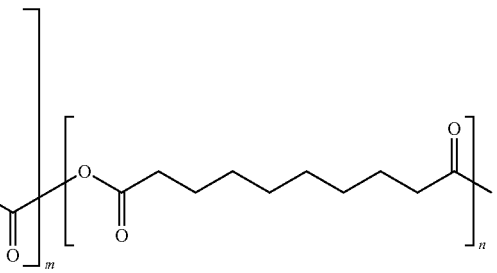

where m and n represent the number of repeating units of each monomer. The fabrication of microspheres and the controlled release of small molecular mass compounds have been reported (Kipper, M. J., Shen, E., Determan, A., Narasimhan, B. (2002) *Biomaterials* 23, 4405-4412; Berkland, C., Kipper, M. J., Kim, K. K., Narasimhan, B., Pack, D. W. (2004) *J. Controlled Release* 94, 129-141).

A key feature of these materials is that their performance in controlled release applications is enhanced by their hydrophobicity. Commonly used polyesters such as poly(lactide) (PLA) and poly(lactide-co-glycolide) (PLGA) have been studied for single-dose vaccines (Alonso, et al. (1994) *Vaccine* 12, 299-306; Men, et al. (1995) *Vaccine* 13, 683-689). Unlike these polyesters, the polyanhydrides of the invention do not swell in the presence of water. This hydrophobic property of the microspheres results in the release of immunogens by a process of surface erosion. More importantly, the exclusion of water from the microsphere aids the stabilization and prolonged immunogenicity of entrapped proteins (Schwendeman, et al. (1995) *Proc. Natl. Acad. Sci. USA* 92, 11234-11238). It has been shown that high-moisture environments can cause proteins such as TT and diphtheria toxoid to form insoluble aggregates, losing about 75% of their solubility, and reducing their immunogenicity, within one week (Schwendeman, et al. (1996) in *New Approaches to Stabilization of Vaccines Potency*, ed. Brown, F. (Karger, Basel), Vol. 87, pp. 293-306).

Another important feature of polyanhydrides of the invention is that the degrading microsphere does not form an acidic microenvironment as extreme as that formed by PLA and PLGA (Goepferich, A., Langer, R. (1993) *J. Polym. Sci. A* 31, 2445-2458; Mäder, et al. (1997) *Polymer* 38, 4785-4794; Kipper, M. J., Narasimhan, B. (2005) *Macromolecules* 38, 1989-1999). This is due in part to the limited solubility of the monomeric dicarboxylic acids released during erosion. For the stabilization of proteins in poly(CPH-SA) microspheres, see Determan, A. S., Nilsen-Hamilton, M., Trewyn, B., Lin, V. S.-Y., Narasimhan, B. (2004) *J. Controlled Release* 100, 97-109. For the ability to purposefully modulate the release profile, by changing the copolymer composition, and thus the hydrophobicity; see Shen, et al. (2002) *J. Controlled Release* 82, 115-125; Larobina, et al. (2002) *AIChE J.* 48, 2960-2970; and Kipper, et al. (2002) *Biomaterials* 23, 4405-4412.

Any suitable and effective ratio of polymer to immunogen can be used in the immunogenic composition. The polymer can be used in an amount ranging from about 1 to about 1,000 times the weight of the immunogen. Typically, the polymer is used in about 20 to about 800 times the weight of the immunogen, about 50 to about 500 times the weight of the immunogen, or about 75 to about 150 times the weight of the immunogen.

The immunogen-loaded microparticles of the invention can be prepared by the water/oil/oil double emulsion technique similar to the method reported by Esparza and Kissel for poly(D,L-lactide-co-glycolide) microspheres (Esparza, I., Kissel, T. (1992) *Vaccine* 10, 714-720). The polymer is dissolved in an organic solvent such as methylene chloride (typically about 20-30 mg/mL). Any suitable solvent can be used to dissolve the polymer. Suitable examples include chlorinated organic solvents such as methylene chloride, chloroform, and carbon tetrachloride. The immunogen is dissolved in pure water (typically about 0.5-2 mg dialyzed and lyophilized immunogen per 25 μL of water). The immunogen solution is added to the polymer solution in a centrifuge tube and immediately emulsified by agitation with a handheld homogenizer. While still homogenizing, silicone oil saturated with methylene chloride is added drop wise to form the microparticles and the mixture is further homogenized.

The loaded microparticles can be precipitated by transferring the double emulsion to a container of cold n-heptane (non-solvent). The mixture is rapidly stirred with an impeller to extract the solvent. Non-solvent can be periodically added to replace volume lost due to evaporation. The microparticles can then be isolated by filtration. The microparticles should be rinsed with additional non-solvent and dried under vacuum to afford a free-flowing powder. An immunogenic formulation for injection can be prepared by suspending the microspheres, optionally with a small bolus of free immunogen, in a 50% cottonseed oil/saline emulsion, saline alone, or saline with a small amount of fetal calf serum.

Microspheres can also be prepared by modifications of the solvent removal technique described above. Suitable modifications may include, but are not limited to a water/oil/water emulsion, a solid/oil/water/emulsion, or spray drying techniques well known to those skilled in the art.

Immunogenic compositions (such as a vaccine) can be formulated and administered in accordance with standard techniques well known to those skilled in the art. For example, a vaccine can be prepared by any suitable method, such as the methods described by Franchini et al., (PCT/US2003/035499), or Caputa et al. (U.S. Pat. No. 5,554,371, for example, at col. 7). Other useful techniques can be used such as those described by Cleary (U.S. Pat. No. 5,846,547, for example, at col. 6-7).

The bioerodible polyanhydride polymers described herein can be used in conjunction with any suitable and effective immunogen. The immunogen can be incorporated into the polymer and can also be provided as a free bolus in addition to the loaded microparticles. The immunogen can be an attenuated, killed, or recombinant antigen. The immunogen can be a single antigen (used for a single disease) or a mixed antigen(s) (used for two or more diseases). The mixed immunogen(s) may be a mixture of two or more antigens, or can be an immunogen that has a plurality of antigenic sites, such as a recombinant protein. The immunogen can be a whole cell, such as a bacterial whole cell, or a portion of a cell, such as an immunogenic protein or polypeptide, or a virus or virion.

The immunogen can be any intracellular pathogen that elicits a $T_H1$ cellular response. The vaccines/immunogenic compositions of the present invention include antigens obtained from or directed against the pathogens responsible for hepatitis, diphtheria, chickenpox, typhoid, pertussis, tetanus, tuberculosis, salmonellosis, cholera, herpes, yellow fever, measles, poliomyelitis, rubella, mumps, rabies, plague, schistosomiasis, influenza, trypanosomiasis, leishmaniasis, leprosy, meningitis, and malaria. More specifically, hepatitis B surface antigen, tetanus toxoid, staphylococcal enterotoxin B toxoid, ricin toxoid, and attenuated influenza virus may be used as antigens for the immunogenic composition, such as a vaccine, of the present invention. The entrapped immunogens may also be used to induce immuno-regulatory mechanisms to control immune-mediated diseases, such as colitis, allergies, and autoimmune diseases.

Other useful immunogens that can be used with the polyanhydride microparticles include HIV envelope polypeptides such as those described by Berman et al. (U.S. Pat. No. 6,042,836), recombinant polypeptides such as those described by Caputa et al. (U.S. Pat. No. 5,554,371), immunologically active proteins such as those described by Motz et al. (U.S. Pat. No. 6,610,301), peptidases or fragments or mutants thereof such as those described by Cleary, et al. (U.S. Pat. No. 5,846,547), recombinant influenza viruses such as those described by Kawaoka, et al. (PCT/US00/09021), smallpox vaccine regimen such as those described by Franchini et al. (PCT/US2003/035499), and combinations of vectors such as those described by Genoveffa et al. (PCT/US01/13968).

The microparticles can be dispersed in an injection medium to prepare an injection formulation for subcutaneous, intramuscular, and intradermal injections. Injection media that can be used in the present invention include buffers, optionally with dispersing agents or preservatives, or both. The injection media can also include mineral oil, cod liver oil, squalene, mono-, di-, or triglycerides, or edible oils such as corn oil, cotton seed oil, olive oil, peanut oil, safflower oil, sesame seed oil, soybean oil, or mixtures thereof.

The example describes the fabrication of TT-loaded polyanhydride microspheres, their in vitro antigen release kinetics, and the in vivo ability to induce an antigen-specific immune response. A dose-dependent inhibition of the immune response by the polymer at high polymer doses was observed, but as the polymer dose was reduced, the inhibition was eliminated and a stimulatory adjuvant effect was observed. No other adverse effects were observed, even when the immune response was inhibited.

The microspheres are capable of inducing a combined $T_H1/T_H2$ immune response when injected intramuscularly, rather than the $T_H2$ immune response that is typical of alum-based vaccines and TT in particular. By injecting the microspheres along with a small bolus of free TT, the $T_H2$ immune response can be selectively inhibited without reducing the overall TT specific antibody production. The bolus of free TT alone is not sufficient to induce a measurable immune response. The mechanisms that govern the deviation of the immune response ($T_H1$ vs. $T_H2$) as defined by changes in the TT specific IgG1 and IgG2a antibody responses are discussed in the examples below.

In the case where a $T_H1$ response is desirable, the inclusion of a small bolus of free immunogen provides activation of the immune response pathway so that the subsequent slow release from the microspheres is more effective. A bolus of about one µg is administered for each milligram of microsphere formulation. Some conditions may require a larger or smaller ratio of free immunogen to microparticle formulation. One or more different immunogens can be included in the bolus.

The polymer microparticles can also be used to prepare an immunogenic composition. The composition can include an immunogen incorporated into an anhydride polymer, preferably with a pharmaceutically acceptable carrier. The composition can optionally include a small bolus of free immunogen.

The immunogen(s) can be any intracellular pathogen that elicits a $T_H1$ cellular response. The immunogen(s) can be an attenuated, killed, or recombinant antigen. The immunogen can be a single immunogen (used for a single disease) or mixed immunogens (used for two or more diseases). The mixed immunogens can be a mixture of two or more immunogens, or the immunogen can be an immunogen that has two or more different types of antigenic sites, such as a recombinant protein. The immunogen can be an intact agent, such as a bacterial whole cell or virion, or a portion of a cell or virus, such as an immunogenic protein polypeptide, oligosaccharide, or oligonucleotide.

The invention will now be illustrated by the following non-limiting Example.

EXAMPLE

Modulation of Immune Response Mechanism

Introduction

This example demonstrates that TT-loaded microspheres preferentially induce both the $T_H1$ and $T_H2$ immune response pathways as evidenced by the IgG2a and IgG1 antibody responses, respectively, when injected intramuscularly into mice. Though the $T_H2$ immune response is higher for some formulations, it can be selectively modulated by altering the immunogenic composition, such as a vaccine, formulation. The ability to induce immune deviation by utilizing the microsphere delivery system can allow for induction of immune responses that are more effective for some viral and other intracellular pathogens. A procedure is described for modulating an immune response by delivering microspheres along with a small bolus of free TT. This ability to adjust the immune response without the administration of additional cytokines or noxious adjuvants is a unique feature of this delivery vehicle and is generally applicable to other vaccines/immunogenic compositions.

This example illustrates the development of a single dose immunogenic composition, such as a vaccine, utilizing bioerodible polyanhydride microspheres that offers the ability to preferentially induce a $T_H1$ immune response, using TT as a model antigen. Single-dose vaccines must provide prolonged exposure to an antigen so that the secondary immune response occurs without the necessity of a second administration. Consequently, the protein must also be stabilized so that an immunogenic/antigenic form is released. This immunogenic composition, such as a vaccine, can allow for targeted delivery of the protein to phagocytes of the immune system to take advantage of their ability to shape the nature of the adaptive immune response.

Mice (C3H/HeOuJ) were inoculated with the microspheres and bled weekly from the saphenous vein for 12 weeks.

Antibody titers were determined by ELISA. The immune response mechanism can be modulated if the microspheres are delivered along with a small bolus of free immunogen. The bolus alone is insufficient to stimulate a sustained immune response, but provides sufficient activation of the immune response pathway that the immune response mechanism is altered.

Materials and Methods

Polymer Synthesis and Characterization

CPH diacid was synthesized by a method similar to that described previously (Conix, A. (1966) *Macromol. Synth.* 2, 95-98) for 1,3bis(p-carboxyphenoxy)propane, using p-carboxy benzoic acid (99+%) and 1,6-dibromohexane (98%). Diacid was purified by recrystallization three times from N-methyl-2-pyrrolidinone. CPH diacid and SA diacid were acetylated to form the prepolymers by refluxing in excess acetic anhydride for 30 minutes (SA) or 60 minutes (CPH) under dry nitrogen sweep. Purification of the crude prepolymers was done using the methods previously reported (Kipper, et al. (2004) *Polymer* 45, 3329-3340).

Prepolymers were mixed in the appropriate mole ratios to obtain 20:80 (CPH:SA) and 50:50 (CPH:SA) copolymers and polymerized by melt polycondensation from acetylated prepolymers as described previously (Kipper, et al. (2002) *Biomaterials* 23, 4405-4412). About 2 ml of acetic anhydride were added to 4 g of prepolymer prior to polymerization to ensure complete acetylation. The polymer was isolated by dissolution in methylene chloride and precipitation in dry hexane (petroleum ether containing 55% n-hexane), dried, and distilled over sodium and benzophenone before use), followed by filtration and drying under vacuum. The polymers were desiccated and stored under dry argon to prevent degradation.

Polymers were characterized by $^1H$ NMR in deuterated chloroform on a Varian VXR 300 MHz spectrometer (Palo Alto, Calif.). Molecular weight was assessed via gel permeation chromatography (GPC) and was performed on a Waters GPC system (Milford, Mass.) using PL Gel columns (Polymer Laboratories, Amherst, Mass.). The poly(CPH-SA) 20:80 copolymer had a weight average molecular weight ($M_w$) of 21,000 and a polydispersity index (PDI) of 2.2. The poly(CPH-SA) 50:50 copolymer had an $M_w$ of 13,000 and a PDI of 2.0. Polymers were stored desiccated under dry argon. Elution times were compared to poly(methyl methacrylate) standards from Fluka (Milwaukee, Wis.). Differential scanning calorimetry (DSC) with a DSC7 calorimeter (Perkin Elmer, Shelton, Conn.) was used to verify that crystalline melting points were the same as reported by Shen, E., Pizsczek, R., Dziadul, B., and Narasimhan, B. (2001) *Biomaterials* 22, 201-210.

Microsphere Fabrication

TT-loaded microspheres were fabricated by a water/oil/oil double emulsion similar to the method reported for poly(D,L-lactide-co-glycolide) microspheres by Esparza and Kissel (Esparza, I., Kissel, T. (1992) *Vaccine* 10, 714-720). Purified TT (1.5 mg/mL, 490 Lf/mL) was purchased from University of Massachusetts Biologic Laboratories (Jamaica Plain, Mass.). Protein was dialyzed against de-ionized water for 48 hours and lyophilized before encapsulation. Polymer (100 mg) was dissolved in methylene chloride (4 mL). Protein (4 mg) was dissolved in nanopure water (100 μL). The protein solution was added to the polymer solution in a 50 mL centrifuge tube and immediately emulsified by agitation at 15,000 rpm with a handheld homogenizer (Tisssue-Tearor™, Biospec Products Inc., Bartlesville, Okla.) for one minute. While still homogenizing, 4 mL of Dow Corning Fluid brand silicone oil, saturated with methylene chloride, was added drop wise to form the microspheres. Homogenization was continued for an additional minute.

To precipitate the microspheres, the double emulsion was transferred to a 400 mL Berzelius beaker containing 300 mL n-heptane on an ice water bath. The heptane was stirred at 300 rpm using a Caframo overhead stirrer (Warrington, Ontario) with a three-inch impeller for three hours to extract the methylene chloride. Heptane was periodically added during the solvent removal to replace the volume lost due to evaporation. The microspheres were isolated by filtration using Whatman #50 filter paper. The beaker and impeller were rinsed several times with fresh heptane to maximize recovery. The microspheres were washed at least three times with 50 mL of heptane to rinse off residual Dow Corning silicone oil, and dried for 24 hours under vacuum. This procedure yielded a free-flowing powder with about 80% of the polymer mass being recovered. Blank microspheres were also fabricated by a similar technique that contained no inner water emulsion.

Microsphere Characterization and In Vitro TT Release Kinetics

The morphology of the microspheres was investigated using scanning electron microscopy using a Hitachi S-2460N scanning electron microscope (San Jose, Calif.). The in vitro protein release kinetics was determined by suspending microspheres (3 to 6 mg) in 2 to 3 ml of 0.1 M phosphate buffer (pH 7.4). Samples of the release buffer (100 μl) were taken periodically and the sample volume was replaced with fresh buffer. Protein concentrations in the buffer solution were measured by micro BCA Protein Assay (Pierce, Rockford, Ill.). Release kinetics experiments were conducted in duplicate.

In Vivo Inhibition of Immune Response

Mice (3 C3H/HeOuJ mice per group, at least 8 weeks of age) were injected intramuscularly in the right quadriceps with free TT and blank 20:80 poly(CPH-SA) microspheres both suspended in a sterile 50% cottonseed oil/saline emulsion. Doses for each group of mice are listed in Table 1. Treatments (dosages) designated 3 mg/3 μg, 1 mg/3 μg, and 0.5 mg/3 μg received the same amount of TT (3 μg), and 3, 1, or 0.5 mg of polymer, respectively. Treatment designated 3 mg/3 μg, day 3, received its TT injection (3 μg) in the same site as the microsphere injection (3 mg) three days later. Treatment designated 3 mg/3 μg, opposite leg, received only TT (3 μg) in the right leg and blank microspheres (3 mg) in the left leg. Treatment designated 0 mg/3 μg received only TT (3 μg). Mice were sampled weekly by collecting 100 μL of blood from the saphenous vein. Serum was separated by centrifugation and stored at −20° C. until assayed for TT specific antibodies. TT specific antibody responses were assessed by enzyme-linked immunosorbent assay (ELISA) (see ELISA Section below). Samples were collected from all three mice at each time point.

TABLE 1

Treatments for inhibition assay and antibody response assay experimental groups

| Inhibition assay | | |
|---|---|---|
| Treatment Designation | Amount of Microspheres Injected & Formulation | Free TT |
| 3 mg/3 μg | 3 mg blank poly(CPH-SA) 20:80 | 3 μg |
| 1 mg/3 μg | 1 mg blank poly(CPH-SA) 20:80 | 3 μg |

TABLE 1-continued

Treatments for inhibition assay and antibody response assay experimental groups

| 0.5 mg/3 µg | 0.5 mg blank poly(CPH-SA) 20:80 | 3 µg |
| 3 mg/3 µg, day 3 | 3 mg blank poly(CPH-SA) 20:80 | 3 µg (on day 3) |
| 3 mg/3µg, opposite leg | 3 mg blank poly(CPH-SA) 20:80 | 3µg (opposite leg) |
| 0 mg/3 µg | None | 3 µg |

Antibody response assay

| Group | Amount of Microspheres Injected & Formulation | Free TT |
|---|---|---|
| 20:80 blank | 0.5 mg blank poly(CPH-SA) 20:80 | None |
| 20:80 blank + bolus | 0.5 mg blank poly(CPH-SA) 20:80 | 0.5 µg |
| 20:80 TT | 0.5 mg TT-loaded poly(CPH-SA) 20:80 | None |
| 20:80 TT + bolus | 0.5 mg TT-loaded poly(CPH-SA) 20:80 | 0.5 µg |
| 50:50 blank | 0.5 mg blank poly(CPH-SA) 50:50 | None |
| 50:50 blank + bolus | 0.5 mg blank poly(CPH-SA) 50:50 | 0.5 µg |
| 50:50 TT | 0.5 mg TT-loaded poly(CPH-SA) 50:50 | None |
| 50:50 TT + bolus | 0.5 mg TT-loaded poly(CPH-SA) 50:50 | 0.5 µg |
| Bolus only | None | 0.5 µg |
| Equivalent dose | None | 10 µg |

Polymer Adjuvanticity and Vaccine Efficacy

In order to assess the ability of the polymers to perform the function of an immune adjuvant, mice (4 to 8 C3H/HeOuJ mice per group, 8 weeks of age) were injected intramuscularly in the right quadriceps with blank microspheres plus a 0.5 µg bolus of free TT suspended in sterile saline containing 0.5% fetal calf serum (FCS) as a surfactant.

The vaccine efficacy was examined by injecting TT-loaded microspheres, or TT-loaded microspheres plus a 0.5 µg bolus of TT. Injections of blank microspheres alone and the bolus alone were used as controls. Treatments for each group are summarized in Table 1. Serum samples were collected and stored as described above. Antibody titers were determined by ELISA (see immediately below). Samples were collected from all mice at each time point.

TT-Specific Enzyme-Linked-Immunosorbent-Assay (ELISA)

The ELISA for antibody titers was performed in 96-well format. Costar ninety-six well high protein binding microtiter plates (Corning, Inc., Corning, N.Y.) were coated with 100 µL phosphate buffered saline (pH 7.4) (PBS) containing 1 µg/ml TT. To remove unbound TT, the plates were washed with PBS containing 0.05% Tween 20 (PBST) and then blocked for two hours at room temperature with PBST containing 2% gelatin and 2% FCS. Serum samples from the individual mice were serially diluted in PBST with 2% FCS and incubated overnight (14 hours) at 4° C. The plates were again washed thrice with PBST followed by addition of 100 µl of PBST with 1% FCS containing alkaline phosphatase-conjugated goat anti-mouse IgG (H&L) (0.5 µg/ml) (KPL, Gaithersburg, Md.). After a 2 hour incubation period, the plates were washed an additional 3 times with PBST followed by the addition of 100 µl of sodium carbonate buffer (pH 9.3) containing 1 mg/ml phosphatase substrate (Sigma 104, Sigma-Aldrich, St. Louis, Mo.) and allowed to react for 1 hour at room temperature. The optical density (OD) of the reaction was measured using a Spectramax 190 Plate Reader (Molecular Devices, Sunnyvale, Calif.). ELISA to determine isotype specific responses (i.e., IgG2a and IgG1) was performed similarly. Detection of isotype specific antibodies was accomplished using alkaline phosphatase-conjugated goat anti-mouse IgG1 or alkaline phosphatase-conjugated goat anti-mouse IgG2a (Southern Biotechnology Associates, Birmingham, Ala.).

Antibody Avidity Index

Avidity was determined by a method similar to that reported by Pullen, et al. (1986) *J. Immunol. Meth.* 86, 83-87. The avidity assays were preformed similarly to the ELISA, with samples and control sera set up in 8 replicates. Following the wash step to remove unbound serum antibody, PBS containing sodium thiocyanate was added to replicate wells in increasing concentrations ranging from 0-3 M. The mixture was incubated for 20 minutes at room temperature. Plates were then washed 4 times with PBST and detection of bound antibody was performed as described above. As a chaotropic agent, sodium thiocyanate promotes dissociation of the antibody from the plate-bound TT. Avidity index is taken as the maximum molarity of sodium thiocyanate that reduces the OD reading by less than 50% of that from the wells treated with PBS alone.

In Vitro Antigen Specific Proliferation Assay

To evaluate the antigen-specific recall response induced by vaccination with a single injection of polyanhydride microspheres, the mice in the group that received the 20:80 TT+bolus regimen were maintained until 28 weeks post immunization and euthanized by $CO_2$ asphyxiation and draining lymph nodes (popliteal and inguinal) were removed using aseptic technique. In addition to this group, peripheral lymph nodes were also harvested from four control groups: The first group (designated "two doses") received two doses of soluble TT (5 µg, 14 days apart). The second group (designated "two doses+ boost") received the same treatment plus an additional 5 mg boost of soluble TT 5 days prior to euthanization. The third group (designated "boost only") received only the 5 µg boost 5 days prior to euthanization. The fourth group of mice was sham injected with saline (designated "naïve"). Treatments for these control groups are summarized in Table 2.

TABLE 2

Treatments for antigen specific proliferation assay control groups

| Group | Soluble TT Injection Schedule | Euthanization |
|---|---|---|
| 2 doses | 5 µg (day 0), 5 µg (day 14) | Day 70 |
| 2 doses + boost | 5 µg (day 0), 5 µg (day 14), 5 µg (5 days prior to euthanization) | Day 70 |
| Boost only | 5 µg (5 days prior to euthanization) | Day 5 |
| Naïve | None | — |

The lymph nodes from all mice in a group were pooled. Single cell suspensions were prepared by homogenizing lymph nodes between two sterilized frosted microscope slides (Fisher) in a small volume of Hank's Balanced Salt Solution (Sigma) supplemented with 5% FCS. Homogenate was transferred to sterile polypropylene tubes, cellular debris was removed by settling, and the cells were washed via centrifugation. The cells were re-suspended in culture medium (cRPMI) consisting of RPMI 1640 containing L-glutamine (Mediatech, Herndon, Va.) and supplemented with 1% non-essential amino acids (Mediatech), 1% sodium pyruvate (Mediatech), 2% essential amino acids (Mediatech), 25 mM HEPES buffer (Mediatech), 100 units/ml penicillin, 0.1 mg/ml streptomycin (Mediatech), 0.05 mg/ml gentamycin (Sigma), 1% L-glutamine (Mediatech), $5 \times 10^{-5}$ M 2-mercaptoethanol (Sigma), and 5% heat-inactivated FCS. Flat-bottomed 96-well microtiter plates were seeded with $5 \times 10^5$ cells in cRPMI at a total volume of 200 µl per well. Cells were stimulated with either concavalin A (Con A, 5 µg/ml, Sigma), which is a non-specific lymphocyte mitogen, or TT at different concentrations (2, 10, 25, or 50 µg/ml). Control wells were given cRPMI alone (i.e., no stimulation). Plates were then incubated for 3 days at 37° C. in 5% $CO_2$ in air. After 3 days, 0.5 μμCi of methyl-[$^3$H]-thymidine (specific activity 6.7 Ci mmole$^{-1}$, Amersham Life Science, Arlington Heights, Ill.) at a concentration of 50 μCi/ml in 10 μl of RPMI 1640 with L-glutamine was added to each well, and the plates were incubated for an additional 18 hours. The contents of each well were harvested onto glass fiber filters, and the incorporated radioactivity was measured by liquid scintillation counting. Each assay was performed in triplicate and data are presented as mean counts per minute ±standard error of the mean (SEM) of the triplicate wells.

Statistical Analysis

Statistical significance (p≦0.05) was determined by performing analysis of variance followed by two-tailed Student's t-tests.

Results

Microsphere Characterization

Figure 1B:
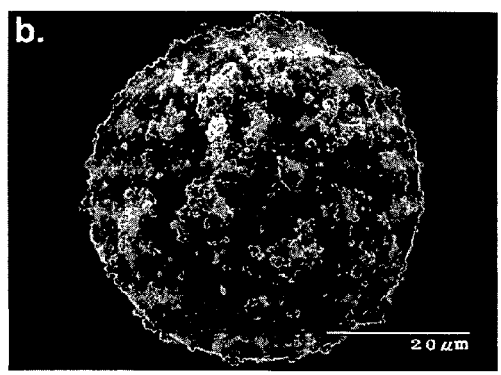
Figure 1C:
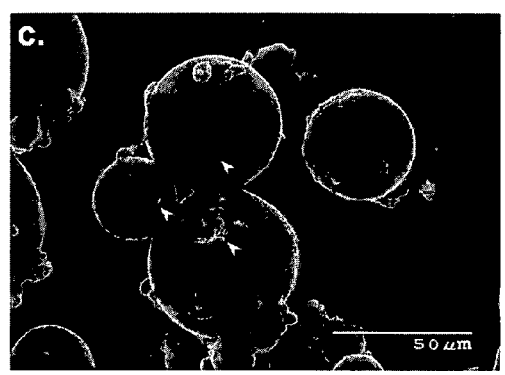
FIG. 1c and FIG. 1d illustrate scanning electron micrographs of TT-Loaded 50:50 poly(CPH-SA) microspheres. The 20:80 copolymer microspheres show small polymer particles flocculated on their surfaces and the 50:50 microspheres show small circular divots (indicated by the arrowheads in FIG. 1c) formed when the loosely adhered clumps of microspheres break apart.
Figure 1D:
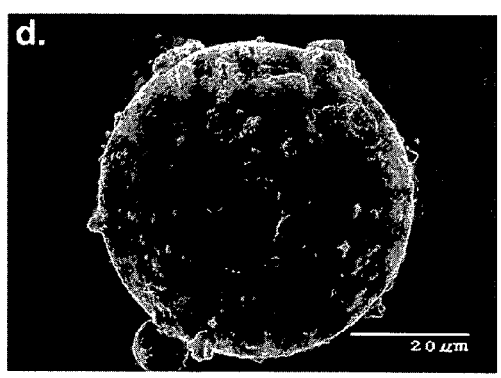

The TT-loaded microspheres had sizes ranging from 10 to 50 μm. Scanning electron micrographs of the TT-loaded poly (CPH-SA) microspheres are shown in FIG. 1a and FIG. 1b. The microspheres had generally smooth surfaces free from pores and cracks. The 20:80 poly(CPH-SA) microspheres behaved as a free-flowing powder with small polymer particles flocculated on the surfaces (FIGS. 1a and b). The poly (CPH-SA) (50:50) microspheres tended to form small loosely adherent clumps as seen in FIG. 1c. This is likely the result of the rubbery nature of the polymer at room temperature ($T_g$<25° C.) (Narasimhan, B., and Kipper, M J (2004) *Adv. Chem. Eng.* 29, 169-218). The fragile adhesions result in small circular divots on the surface of the microspheres when the clumps break apart (indicated by the arrowheads in FIG. 1c).

Figure 2:
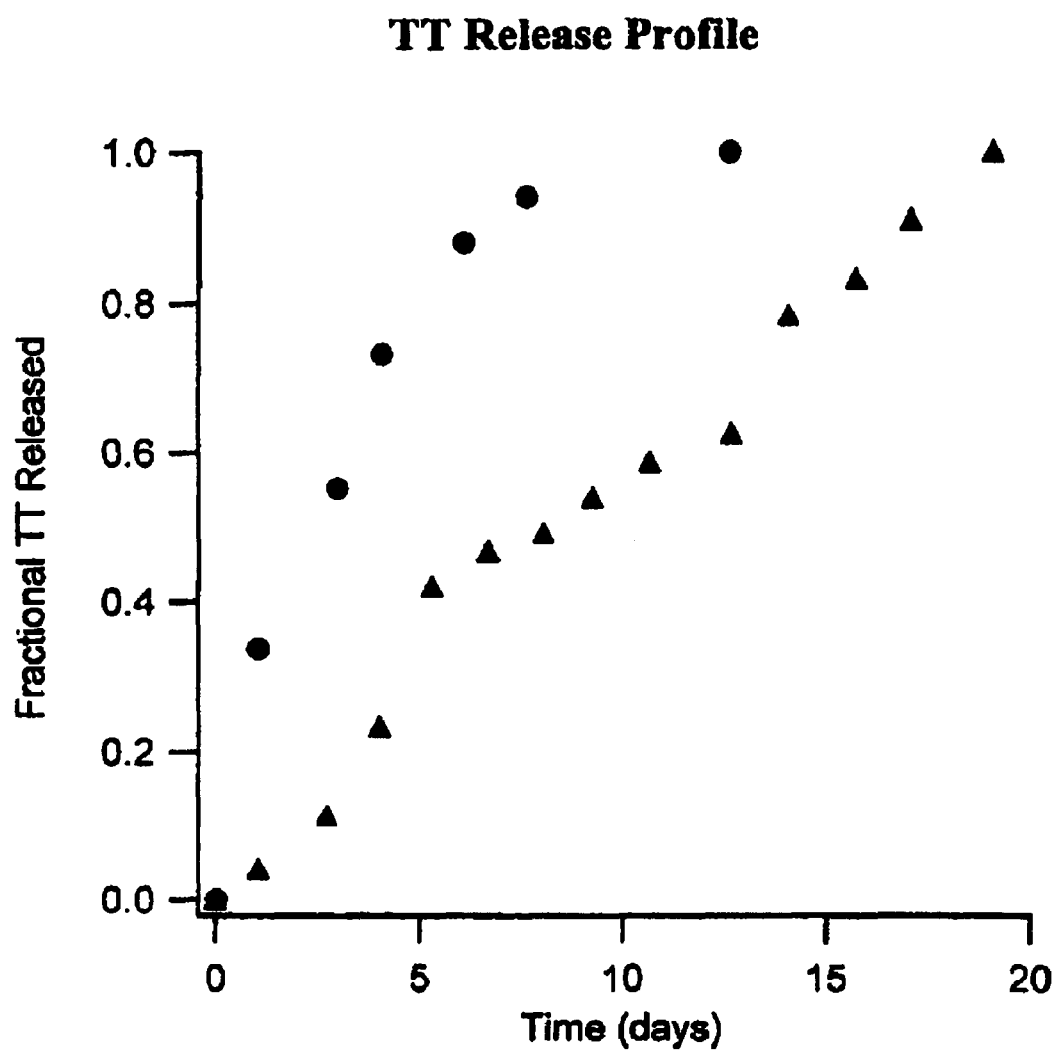
FIG. 2 illustrates in vitro TT release profiles for TT-loaded poly(CPH-SA) 20:80 (●) and 50:50 (▲) microspheres.

The in vitro release profiles for TT-loaded microspheres are shown in FIG. 2. The loading efficiency was calculated from the total mass of protein released. The loading efficiency (mass of protein released per mass of protein used during microsphere fabrication) was 34% for the 20:80 copolymer and 51% for the 50:50 copolymer, leading to loading values (mass of protein encapsulated per mass of microspheres) of 1.4% and 2%, respectively. As anticipated, increased hydrophobicity of the polymer (i.e., higher mole fraction of CPH) decreased the release rate. Zero-order (uniform) release of the protein was obtained in both cases. The poly(CPH-SA) 20:80 copolymer released greater than 90% of the protein within one week, while the poly(CPH-SA) 50:50 copolymer released all the protein over a period of about 19 days.

Microspheres were treated as sterile after isolation from methylene chloride and heptane, both strong solvents. In vitro cell culture experiments using TT-loaded or blank microspheres did not induce demonstrable (i.e., non-specific) stimulation, a sign of significant endotoxin contamination or any signs of bacterial growth (lab observation, data not shown). In addition, mice were observed 12 to 24 hours post-injection and no clinical signs of endotoxemia were observed (e.g., ruffled fur, weepy eyes, hunched appearance, and/or loose stools).

Inhibition of Immune Response

Figure 3:
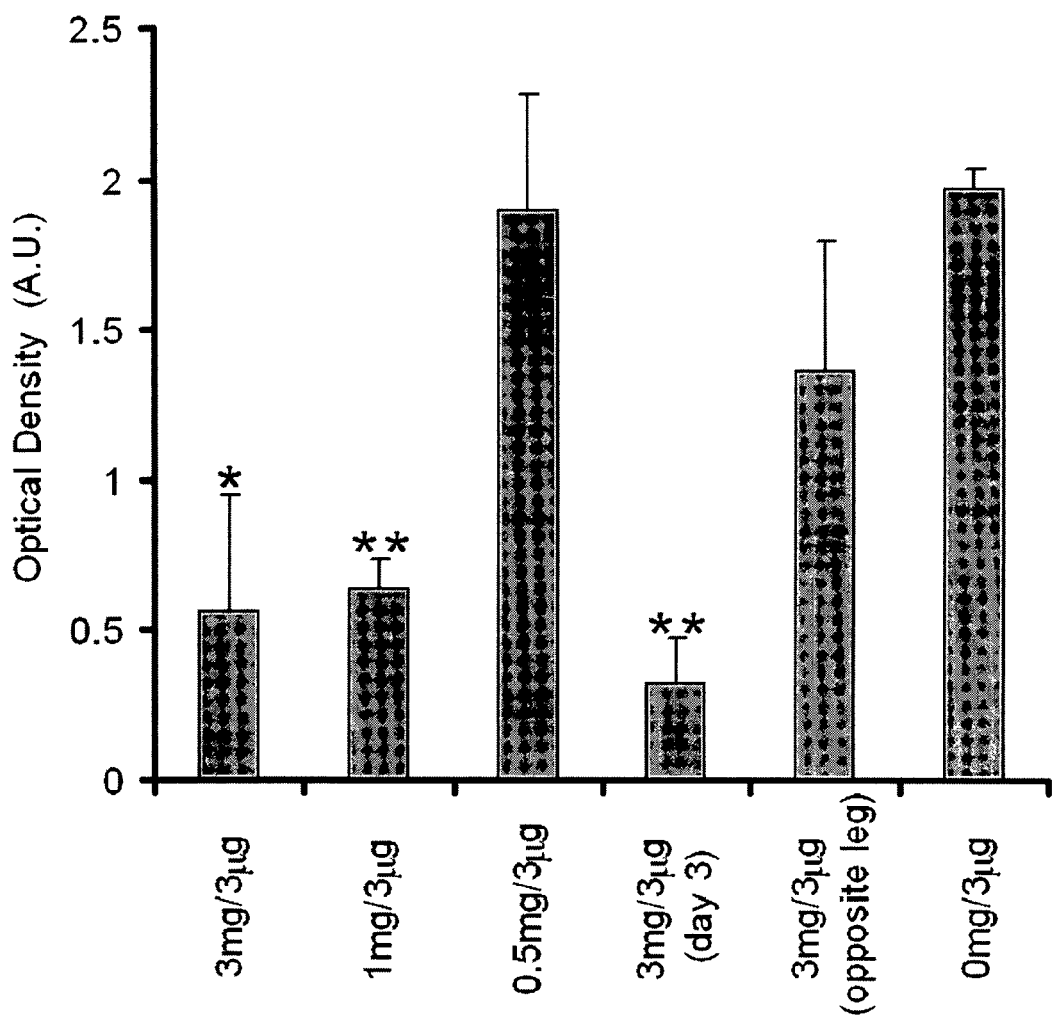
FIG. 3 illustrates the measurement of serum anti-tetanus toxoid (TT) IgG antibody responses following immunization of free TT in the presence of blank microspheres. As described below in the Materials and Methods section of the Example, an ELISA method was used to evaluate the inhibition of TT-specific IgG induction in mice (4 weeks post immunization, 1:400 serum dilution). All groups received the same dose of free TT (3.0 μg). Treatments for each group are detailed in Table 1. Error bars represent S.E.M. Statistical difference from the group receiving the 0 mg/3 μg treatment is indicated by *, indicating $p<0.05$, and **, indicating $p<0.01$.

To determine whether the polymer itself would inhibit the induction of an immune response, blank poly(CPH-SA) 20:80 microspheres were injected intramuscularly at different doses, along with 3 μg of free TT into groups of 3 mice and the production of serum antibody was assessed 4 weeks later (FIG. 3). The treatments for each group are listed in Table 1 and are designated by the weight (mg) of blank microspheres and the amount of TT administered (i.e. milligrams of blank microspheres/micrograms of TT). The OD values obtained from the ELISA are shown in FIG. 3. Groups receiving the 3 mg/3 μg, 1 mg/3 μg, and 3 mg/3 μg (day 3) treatments failed to develop significant antibody responses compared to the group that received only TT (0 mg/3 μg) (p<0.05, p<0.01, p<0.01, respectively). However, when the polymer dose was reduced to 0.5 mg (0.5 mg/3 μg) or when the polymer and TT are delivered at separate injection sites [3 mg/3 μg (opposite leg)] the inhibition of the immune response was obviated. These results demonstrated that the polymer induced a localized, dose-dependent inhibition of the antibody response, and suggests that the observed inhibition was not systemic. This observation is consistent with previous reports investigating adjuvant activity of synthetic muramyl dipeptide in vivo (Warren, et al. (1986) *Annu. Rev., Immunol.* 4, 369-388). This result is also consistent with a recent in vitro study to stimulate cultures of human macrophages (Rimaniol, et al. (2004) *Vaccine* 22, 3127-3135) that show more than 10 μg/ml alum induced 50% cell mortality whereas 5 μg/ml induced less than 30% cell mortality and induced changes in cell surface marker expression (MHC II) considered to be indicative of an activated phenotype. Because no inhibition was observed for the mice receiving only 0.5 mg of polymer, this dose was chosen as the optimal dose for a single injection and used in all subsequent experiments. This is consistent with the in vivo dose extrapolated from human studies evaluating the weight of polymer per kilogram body weight for drug delivery (Katti et al., *Adv. Drug Deliv. Rev.* (2002) 54, 933-961). While several studies have evaluated the effect of polyanhydrides on various tissues for drug delivery, the effect of polyanhydrides on activation of the immune system has not been reported previously (see Katti, et al. (2002) *Adv. Drug Delivery Rev.* 54, 933-961; Tamargo, et al. (1989) *J. Biomed. Mater. Res.* 23, 253-266; Laurencin, et al. (1990) *J. Biomed. Mater. Res.* 24, 1463-1481; Brem, et al. (1992) *J. Controlled Release* 19, 325-350; and Brem, et al. (1989) *Sel. Canc. Ther.* 5, 55-65).

Polymer Adjuvanticity and Vaccine Efficacy

The polymer adjuvanticity was assessed by injecting groups of 4 to 8 mice with blank microspheres plus a suboptimal dose (0.5 μg bolus) of free TT (designated "20:80 blank+bolus" and "50:50 blank+bolus") or 0.5 μg bolus alone (designated "bolus only"). The vaccine efficacy (ability to induce a sustained secondary immune response) was assessed by injecting mice with TT-loaded poly(CPH-SA) 20:80 or 50:50 microspheres (designated "20:80 TT" and "50:50 TT") or TT-loaded microspheres with a 0.5 μg bolus of free TT (designated "20:80 TT+bolus" and "50:50 TT+bolus") in a single immunization. Control groups received only blank microspheres (designated "20:80 blank" and "50:50 blank") or an equivalent dose of free TT (designated "equivalent dose"). The treatments (dosages) received by each group are listed in Table 1. In all formulations containing the bolus with microspheres, they are administered together in a single injection. The ELISA for measuring TT-specific IgG was performed on serum samples collected weekly from all mice in each group. FIG. 4 shows the antibody titers for each of these experimental and control groups over the twelve weeks of this study. All of the mice given only 20:80 blank or 50:50 blank microspheres (○) or the bolus only (+) show no significant antibody response. However, an adjuvant effect was observed when a 0.5 μg bolus of TT was delivered along with blank microspheres (20:80 blank+bolus and 50:50 blank+ bolus, ●). The adjuvant effect is significant at 6 weeks for the 20:80 blank+bolus group (p=0.009) but by week 12 the statistical significance of the adjuvant effect is only marginal (p=0.087). The observed adjuvant effect for the 50:50 blank+ bolus group is not statistically significant at any time point ($0.05 < p < 0.2$ for all time points beyond 3 weeks).

All of the mice receiving the TT-loaded microspheres (20:80 TT, 20:80 TT+bolus, 50:50 TT, and 50:50 TT+bolus, □ and ■ in FIG. 4) exhibited an antibody response. The 50:50 TT and 50:50 TT+bolus treatments induced an antibody response that was comparable to the responses of mice immunized with 10 µg TT (equivalent dose, X), but the 20:80 TT and 20:80 TT+bolus treatments induced titers that are three to five times greater than those induced by the equivalent dose of free TT. (At week 12, $p=0.011$ and 0.055 for the 20:80 TT and 20:80 TT+bolus treatments respectively, compared to the equivalent dose.) The antibody responses of the groups receiving 20:80 TT and 50:50 TT indicate that immunogenic protein was released from the microspheres. The prolonged exposure to immunogenic TT provided by the microspheres was sufficient to induce an antibody response, which was sustained over at least 12 weeks. Antibody titers for the 20:80 TT, 20:80 TT+bolus, 50:50 TT, and 50:50 TT+bolus remained elevated (e.g., above $10^4$) for 28 weeks (data not shown).

Immune Response Modulation

Figure 4A:
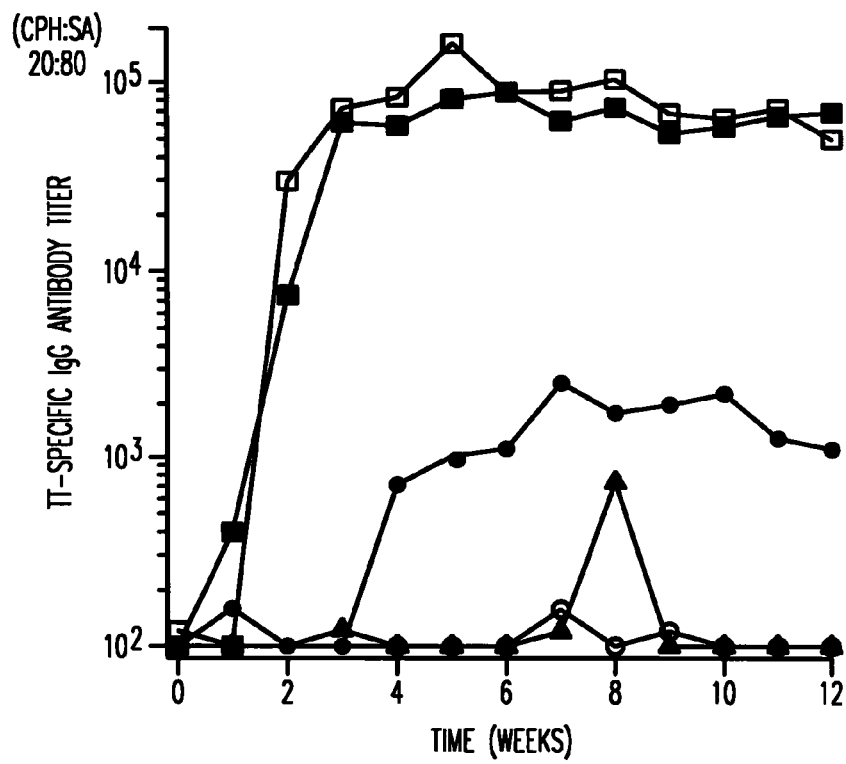
FIG. 4 illustrates average antibody titers for groups which received poly(CPH-SA) 20:80 microspheres (FIG. 4A) and groups which received poly(CPH-SA) (50:50) microspheres (FIG. 4B). The symbols used are: 20:80 blank or 50:50 blank microspheres (○); bolus only (▲); 20:80 blank+0.5 μg bolus and 50:50 blank+0.5 μg bolus (●); 20:80 TT, 20:80 TT+bolus, 50:50 TT, and 50:50 TT+bolus (□ and ■). Treatments for each group are detailed in Table 1. Error bars represent S.E.M. Both polymers provide an adjuvant effect, enhancing the response when blank microspheres are delivered along with the 0.5 μg bolus (●). The TT-loaded poly(CPH-SA) 20:80 microspheres provide a superior antibody titer to an equivalent dose of free TT. (Compare □ and ■ to x in FIG. 4A.)
Figure 4B:
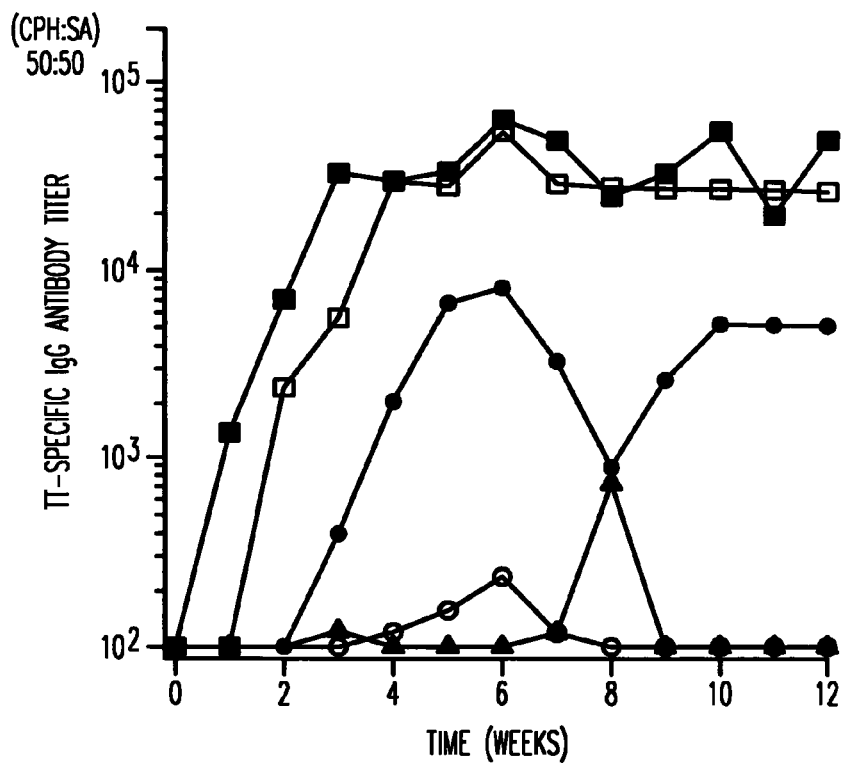
Figure 5:
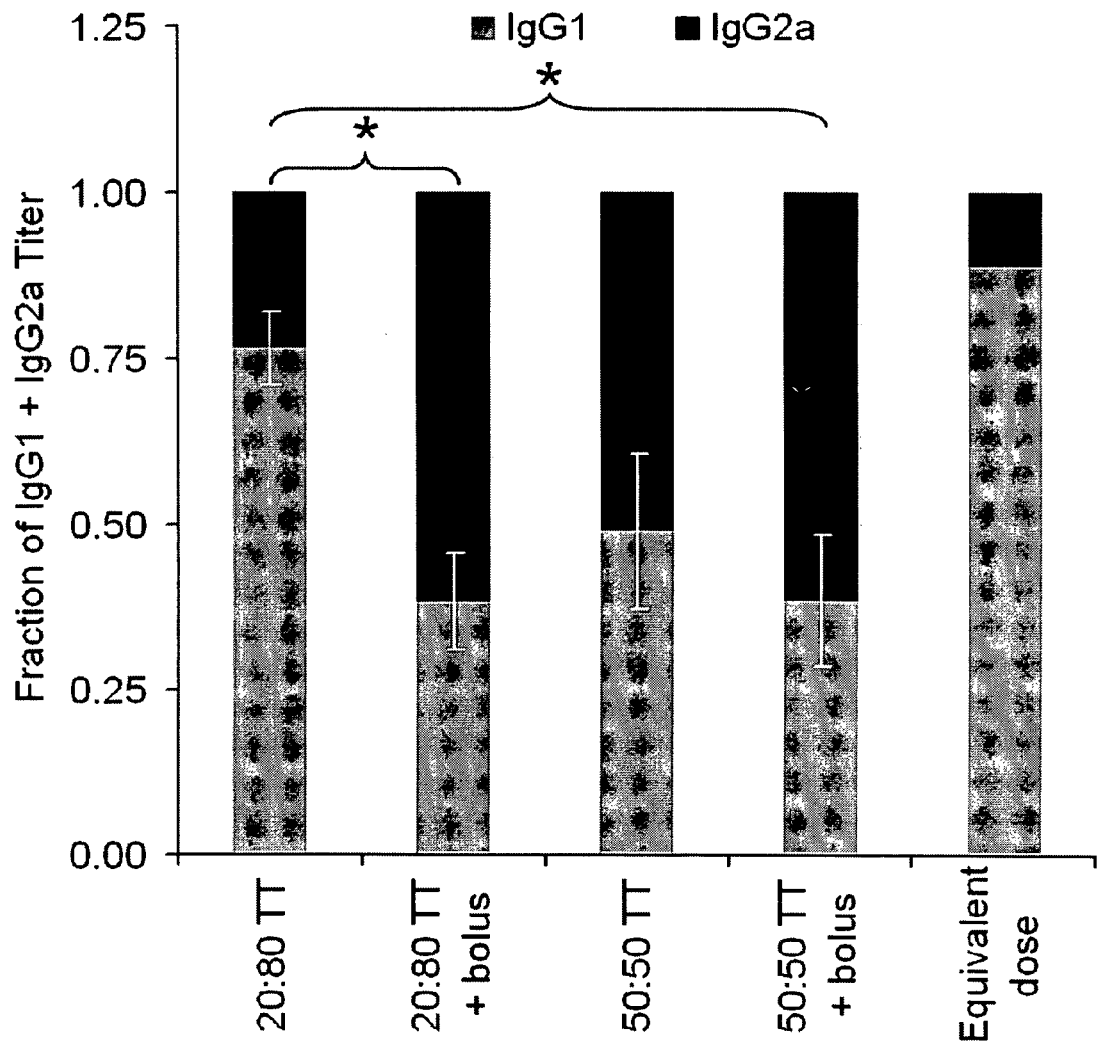
FIG. 5 illustrates IgG specific isotypes of the TT-specific antibody response. Treatments for each group are detailed in Table 1. Error bars represent S.E.M. Fraction of the IgG1 and IgG2a TT-specific antibody titers at week 12 for the 20:80 TT, 20:80 TT+bolus, 50:50 TT, 50:50 TT+bolus, and equivalent dose treatment groups. While the TT-loaded poly(CPH-SA) (20:80) microspheres result in a $T_H2$ response, the addition of a 0.5 μg bolus of free TT results in a balanced ($T_H0$) response. The 20:80 TT treatment group is statistically different ($p<0.05$) from the 20:80 TT+bolus and the 50:50 TT plus bolus treatment groups as indicated by *.

The 0.5 µg bolus of free TT administered in conjunction with the TT-loaded microspheres (20:80 TT+bolus and 50:50 TT+bolus) did not affect the magnitude of the TT-specific IgG antibody titer compared to mice that received the 20:80 TT and 50:50 TT treatments without the bolus. However, the presence of the free TT administered in conjunction with the TT-loaded microspheres did modulate the nature of the immune response as demonstrated for the mice receiving 20:80 TT+bolus. In order to evaluate the nature of the immune response, TT-specific IgG1 and IgG2a antibody levels were measured by ELISA using serum samples collected at four, eight, and twelve weeks post immunization. FIG. 5 shows the relative fractions of the IgG1 and IgG2a TT-specific antibody titers for the 20:80 TT, 20:80 TT+bolus, 50:50 TT, 50:50 TT+bolus, and equivalent dose treatments at 12 weeks post-immunization. Serum antibody responses for the 20:80 TT treatment were characterized by a strong preference for IgG1 production indicating a dominant $T_H2$-type immune response. However, when the 0.5 µg bolus of free TT was delivered along with the TT-loaded microspheres (20:80 TT+bolus and 50:50 TT+bolus) the resultant immune response was balanced as demonstrated by similar IgG1 and IgG2a antibody titers (i.e., $T_H0$ immune response). The difference in the relative fraction of IgG1 was statistically significant for the 20:80 TT treatment group compared to the 20:80 TT+bolus and 50:50 TT+bolus treatment groups ($p<0.05$). This outcome corresponded to a reduction in the IgG1 titer compared to the 20:80 TT treatment while the IgG2a antibody titer was not significantly affected by the addition of the bolus (data not shown). Although the addition of the bolus reduced the IgG1 titer, there was no decrease in the total TT-specific IgG titer (FIG. 4A). The IgG1 fraction response for the 50:50 TT treatment indicates a balanced immune response, however, this treatment also resulted in lower overall TT-specific IgG titers (FIG. 4B) and weaker avidity antibody (see below). Thus, we attributed the apparent $T_H1$-$T_H2$ balance shown in FIG. 5 for this group to a weak antibody response rather than immune modulation.

Most vaccines currently approved for human use contain an alum-based adjuvant (Gupta, R. K.; Siber, G. R. (1994) *Biologicals* 22, 53-63), which typically induces a $T_H2$ dominant response (Singh, M.; O'Hagan, D. T. (2003) *Int. J. Parasitology* 33, 469-478). The $T_H1$ immune response is a beneficial response for enhanced immunity to viral or other intracellular pathogens and the $T_H2$ immune response has been implicated in the development of allergies (see Barth, et al. (2003) *Clin. Exp. Immunol.* 134, 78-85; Romagnani, S. (2004) *Immunology* 112, 352-363; Kim, et al. (2003) *J. Laryngol. Otol.* 117, 946-950; and Cottrez, et al. (2000) *J. Immunol.* 165, 4848-853). Thus, the ability to inhibit preferentially or regulate preferentially the $T_H2$ immune response is a valuable and unique feature of this delivery vehicle.

In Vivo Antibody Avidity

Figure 6:
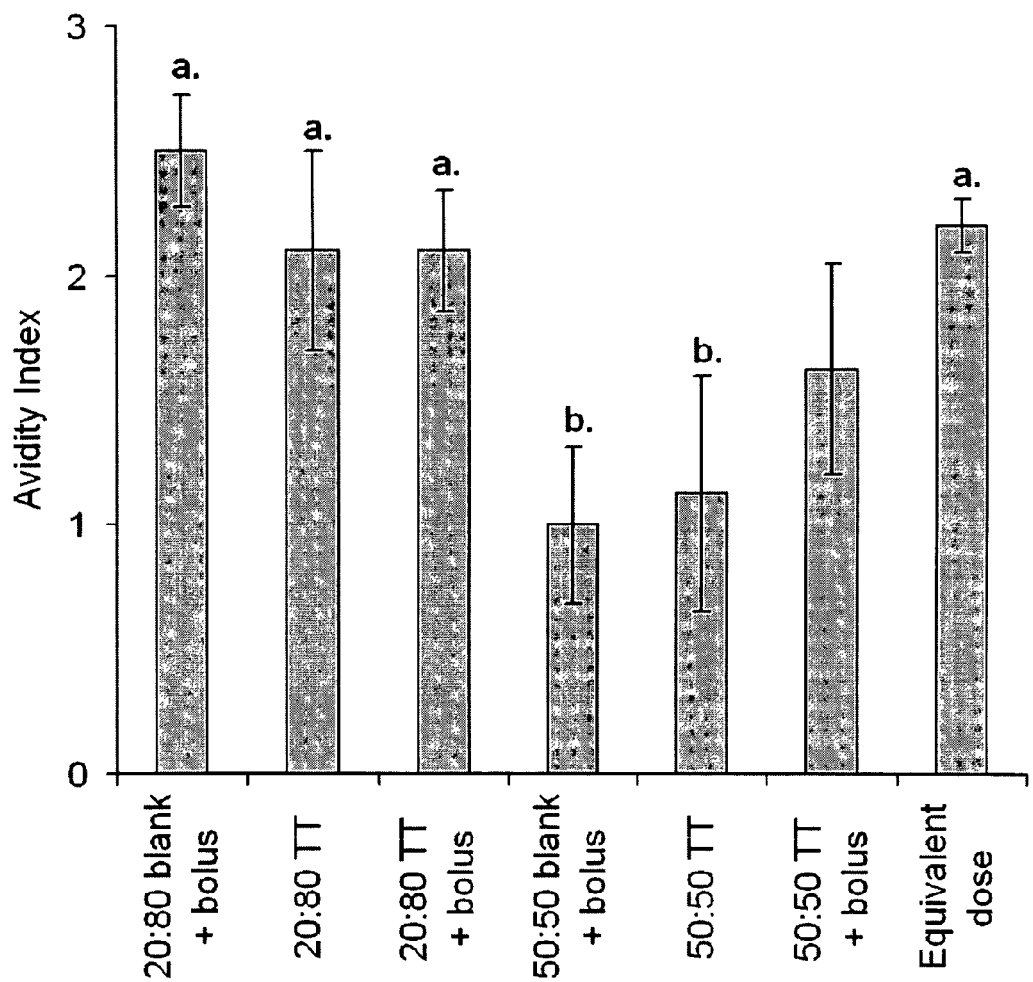
FIG. 6 illustrates the antibody avidity index for groups shown in FIG. 5 and the 20:80 blank+bolus and 50:50 blank+bolus treatment groups. Histogram bars marked with letters are statistically different from bars marked with other letters ($p<0.05$), but not statistically different from bars marked with the same letter ($p>0.1$)

In order to characterize more fully the efficacy of the immune response, the avidity of the antibody was assessed for the mice receiving the 20:80 blank+bolus, 20:80 TT, 20:80 TT+bolus, 50:50 blank+bolus, 50:50 TT, 50:50 TT+bolus, and equivalent dose treatments. The avidity index is shown in FIG. 6. A higher avidity index indicates a higher binding affinity of the antibody for its ligand (i.e., TT) (Pullen et al. ((1986) *J. Immunol. Meth.* 86, 83-87). Higher affinity antibodies show greater protection in vivo (Zinkernagel, R M. (2002) *Curr. Opin. Immunol.* 14, 523-536). All of the mice immunized with poly(CPH-SA) 20:80 microspheres developed antibody responses with higher avidity indices than the animals immunized with poly(CPH-SA) 50:50 microspheres. The avidity indices for 20:80 blank+bolus, 20:80 TT, 20:80 TT+bolus, 50:50 TT+bolus, and equivalent dose treatment groups were not statistically different from each other ($p>0.10$), whereas, the avidity indices for the groups receiving the 50:50 blank+bolus and the 50:50 TT treatments were significantly less than the avidity indices for the groups receiving 20:80 blanks+bolus, 20:80 TT, 20:80 TT+bolus, 50:50 TT+bolus or the equivalent dose treatments ($p<0.05$).

As demonstrated by the 20:80 blank+bolus treatment group, avidity and antibody titer are not necessarily correlated; however, a high correlation between avidity and protection has been reported by Zinkernagel. Our results show that poly(CPH-SA) 20:80 microspheres produced both high avidity antibody and higher overall IgG titers than the poly (CPH-SA) 50:50 microspheres. Furthermore, as shown above, poly(CPH-SA) 20:80 formulations can alter the $T_H1$-$T_H2$ bias in the resulting immune response by the addition of a small bolus of free immunogen. The comparatively lower total IgG titers for the poly(CPH-SA) 50:50 microspheres (FIG. 4B) and the lower avidity (FIG. 6) suggested that these formulations provided a weaker overall antibody response.

In Vitro Antigen Specific Proliferation Assay

Figure 7:
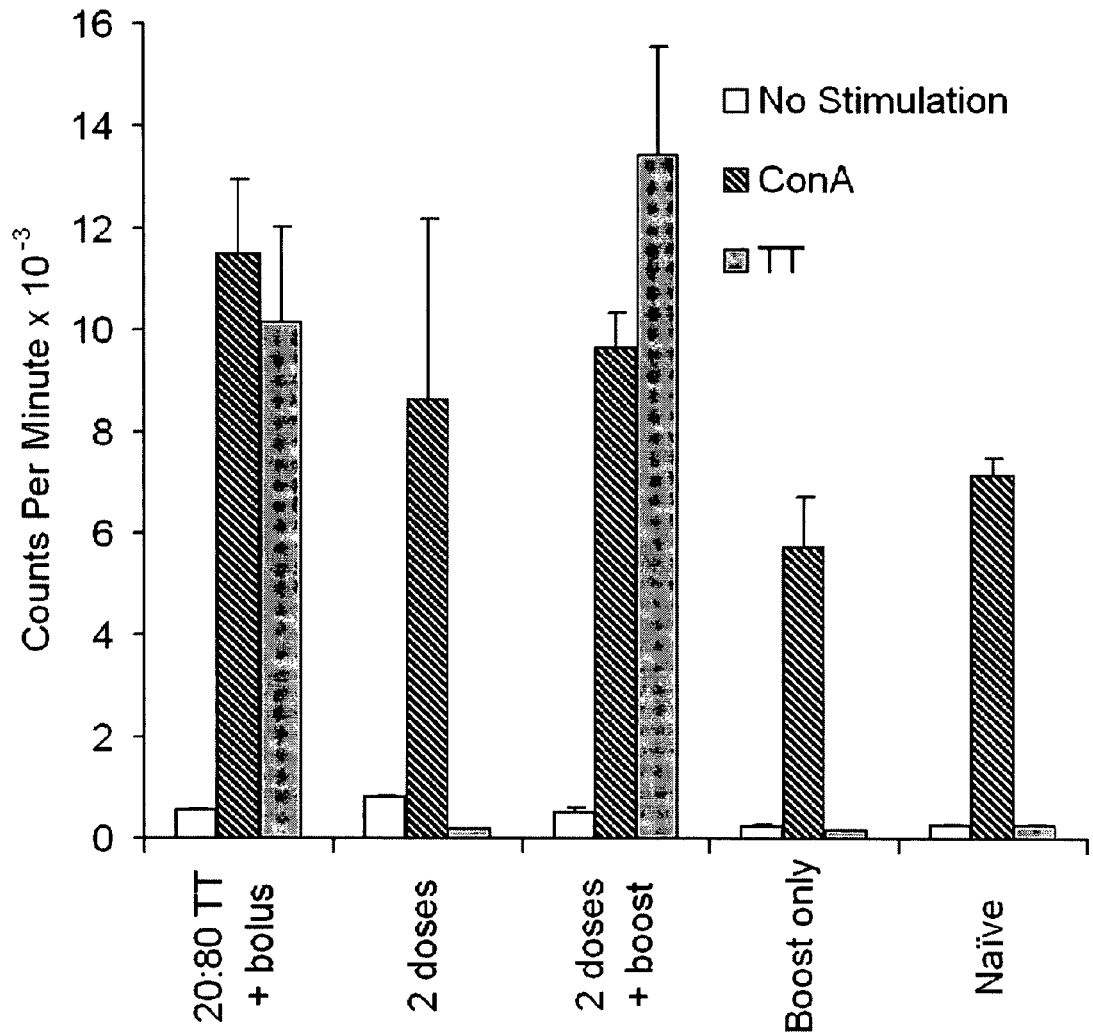
FIG. 7 illustrates antigen specific proliferation of peripheral lymph node lymphocytes isolated from immunized mice. Treatment regimens are detailed in Table 2. Lymph nodes were harvested 28 weeks after immunization from mice in the 20:80 TT+bolus, 2 doses (5 μg soluble TT, 14 days apart) 8 weeks after second injection, 2 doses+boost (5 μg, of soluble TT 14 days apart plus an additional 5 μg boost of TT 5 days prior to euthanization), the boost only (5 μg of soluble TT 5 days prior to euthanization), and naïve (no TT at all) treatment groups. Cells were stimulated in vitro for 72 hours with medium alone (no stimulation), 5 μg/ml concanavalin A (ConA), or 25 μg/ml TT (TT). Data are presented as mean counts per minute ±S.E.M for triplicate wells following incorporation of $^3$H-thymidine.

The high titers of high-avidity antibody produced by the mice in the 20:80 TT+bolus treatment group, combined with the immune deviation (i.e., switch from a dominant $T_H2$ to a balanced $T_H0$ response) for this group (FIG. 6) prompted us to investigate whether a memory recall response was also induced in these animals. The animals in this group were maintained for 28 weeks post-immunization, at which time they were euthanized and the draining lymph nodes (popliteal and inguinal) were harvested. For comparison, mice immunized with TT only, as outlined in Table 2, were euthanized and draining lymph nodes harvested at approximately 8 weeks post-immunization, when cellular recall responses are maximal. Lymphocyte cultures were prepared and stimulated in vitro with medium alone (no stimulation), Con A (non-specific lymphocyte mitogen), or TT. Proliferation was assessed by $^3$H-thymidine incorporation. Lymph node cells collected from all treatment groups demonstrated the capacity to proliferate when stimulated by ConA. However, only cultures from mice that received two doses of soluble TT plus a boost 5 days prior to euthanization (2 doses+boost) and mice that received the 20:80 TT+bolus treatment proliferated in response to TT (FIG. 7). For these two groups, counts per minute ranged from 10,147 to 16,650 in response to stimulation with the differing doses of TT (2-50 μg/ml) (FIG. 7). The proliferative response of cells harvested from the 20:80 TT+bolus treatment group was not statistically different from the proliferative response of cells harvested from the mice immunized with 2 doses of TT and received the boost 5 days prior to euthanization (p>0.1). The cellular responses of mice which received only the boost 5 days prior to euthanization (boost only) were not statistically different from those observed for cells recovered from mice that received a sham immunization (naïve) or mice immunized with 2 doses of soluble TT but were not given the 5 μg boost (2 doses) (p>0.05).

Table 3 presents a qualitative summary of the key results. Vaccinating with either the TT-loaded 20:80 or 50:50 microspheres results in overall TT-specific IgG titers that are at least comparable to vaccination with TT alone, regardless of whether or not the bolus of free TT is included in the formulation. However, the TT-loaded 50:50 microspheres result in lower antibody avidity unless the bolus is added. The TT-loaded 20:80 microspheres result in superior TT-specific IgG production and high avidity antibody. The 20:80 formulations also offer the potential to modulate the immune response mechanism reflected in the change in the dominant IgG isotype. Finally, a proliferative recall response indicating immunological memory can be induced by immunization with a single dose of the TT-loaded 20:80 microspheres with a bolus of free TT. This is a striking result because a total of 2 doses plus a recent boost of TT is required in order to obtain a similar response with free TT.

TABLE 3

Summary of immune responses to TT in mice following different immunization regimens utilizing polyanhydride microspheres

|  | Soluble TT | 20:80 TT | 20:80 TT + bolus | 50:50 TT | 50:50 TT + bolus |
|---|---|---|---|---|---|
| TT-specific IgG titer | ++[1] | +++ | +++ | ++ | ++ |
| Antibody avidity | ++[2] | ++ | ++ | + | ++ |
| Immune response profile | $T_H2$ | $T_H2$ | $T_H0$ | $T_H0$ | $T_H0$ |
| Proliferation | Yes (boost required[3]) | Not tested | Yes (boost not required) | Not tested | Not tested |

[1] magnitude of the immune response relative to mice receiving saline or blank microspheres (i.e., negative controls)
[2] magnitude of the avidity index relative to that of the mice receiving the 0.5 μg suboptimal dose of free TT
[3] Boost: 5 μg soluble TT administered intramuscularly 5 days before cell harvest Mechanism of Action The exact mechanism by which the microsphere/bolus combination affects the induction of a balanced $T_H1$-$T_H2$ immune response as opposed to a dominant $T_H2$ immune response observed with other vaccine regimens is not clear, and multiple mechanisms may be involved. Rotta et al. ((2003) *J. Exp. Med.* 198, 1253-1263) have shown that the maturation of monocytes into antigen presenting cells (APCs) can be inhibited or delayed by bacterial factors such as lipopolysaccharide. In their study, the maturation of APCs was mediated (though not exclusively) through the toll-like receptor-4 (TLR4), an innate immunity receptor. Seong and Metzinger recently proposed that the promiscuity of hydrophobic receptors, and consequently the recognition of many hydrophobic ligands, plays a key role in their effectiveness as inducers of immunity (Seong, S. and Metzinger, P. (2004) *Nat. Rev. Immunol.* 4, 469-478). This likely explains why effective adjuvants are often hydrophobic in nature, oil- or lipid-based. The ability of the host to activate innate immune mechanisms (e.g., adjuvant responses) by recognition of hydrophobic moieties often contributes to the development of more robust antibody- and cell-mediated immune responses (Seong, S. and Metzinger, P. (2004) *Nat. Rev. Immunol.* 4, 469-478).

With these observations in mind, we hypothesize a mechanism for the immune modulation observed following vaccination with the 20:80 TT+bolus treatment compared to mice vaccinated with 20:80 TT or equivalent dose treatments. This hypothesized mechanism should in no way be construed as limiting. When TT-loaded poly(CPH-SA) microspheres are injected, the hydrophobic microspheres, possibly through activation of pattern recognition receptors, delay the maturation of monocytes into mature antigen presenting dendritic cells (DCs). As the polymer erodes and releases TT, the inflammatory response resulting from the injection of hydrophobic microspheres wanes and mature DCs ultimately migrate to the draining lymph node (DLN) to present the antigen to T cells. In this case, the immune response is antigen driven and results in a $T_H2$ dominant response.

However, when free TT is delivered along with the microspheres, some APCs will pinocytose free TT and migrate to the DLN, presenting the antigen in the context of the inflammatory chemokines (e.g., IL-12) produced by those APCs that have interacted with or phagocytosed microspheres. IL-12 preferentially stimulates $T_H1$ cells that produce interferon-γ in sufficient quantity to regulate IgG1 production. In this case, both IgG1 and IgG2a are produced and neither isotype dominates (i.e., IgG1 fraction is near 0.5), resulting in the $T_H0$ phenotype observed for the group immunized with the 20:80 TT+bolus treatment.

The overall magnitude and immunological bias of an immune response is often regulated by the vigor of the APC response (see Banchereau, J. and Steinman, R M. (1998) *Nature* 392, 245-252 and Van der Kleij, D. and Yazdanbakhsh, M. (2003) *Eur. J. Immunol.* 33, 2953-2963). The production of cytokines by APCs will facilitate the induction of $T_H1$ (IL-12, IL-18) or $T_H2$ (IL-4, IL10) biased immune responses (Banchereau, supra). In addition, the hydrophobic nature of the adjuvant plays a key role in the maturation of the APC and the eventual bias of the immune response (Van der Kleij, supra and Hunter, et al. (1981) *J. Immunol.* 127, 1244-1250). In this regard, the relative hydrophobicity of the poly(CPH-SA) microspheres in combination with the relative rate of protein release modulated the magnitude and direction of the immune response. Based on the results shown in FIGS. 2 and 4B, the poly(CPH-SA) 50:50 microspheres do not release sufficient immunogenic protein in a short enough time span in order to induce a strong T helper cell response, which would be characterized by no preference for IgG1 or IgG2a production and weak avidity antibody. A second possible mechanism for the lower antibody titer could be related to the increased hydrophobicity, affecting the function of the DCs resulting in the induction of a poor immune response or a regulatory T cell response (Van der Kleij, supra). This is demonstrated in the lower antibody titers for mice immunized with the 50:50 TT and 50:50 TT+bolus formulations compared to groups of mice immunized with the 20:80 TT and 20:80 TT+bolus formulations (FIG. 4B). A final explanation for the reduced titer and avidity index obtained for antibody responses induced in mice vaccinated with the formulations based on poly(CPH-SA) 50:50 is related to the stability of the encapsulated TT. We have previously demonstrated that as the CPH content of poly(CPH-SA) copolymers is increased, the stability of encapsulated proteins is reduced (Determan, et al. (2004) *J. Controlled Release* 100, 97-109). Thus, the TT released from the poly(CPH-SA) 50:50 microspheres in this study may have lost immunogenic epitopes associated with the primary or secondary structure, thereby resulting in a less vigorous antibody response.

However, the addition of the free TT bolus to the poly (CPH-SA) 50:50 microspheres resulted in an avidity index similar to that obtained with the formulations based on poly (CPH-SA) 20:80 and the 10 μg dose of free TT (FIG. 6). In addition, the formulations based on the poly(CPH-SA) 50:50, both with and without the bolus, resulted in a balanced immune response (i.e., $T_H0$) as demonstrated by the fraction of IgG1 and IgG2a TT-specific antibody titers. This suggests that the nature of the immune response (i.e., antibody titers, isotypes, avidity) can be modulated by the polymer hydrophobicity and the immunogenic composition, such as a vaccine, formulation (i.e., bolus) allowing for the rational design of effective vaccines.

There is evidence of T cell involvement in the immune response to TT following vaccination with the TT-loaded microspheres. Protein antigens induce weak antibody responses in the absence of adequate CD4 T cell help (Janeway, et al. *Immunobiology: the immune system in health and disease*, New York: Garland Publishing (2001)). Our evidence of high titer IgG (FIG. 4), no measurable anti-TT IgM (data not shown), and high avidity antibody (FIG. 6) detected in the serum of mice immunized with the 20:80 TT or equivalent dose treatments all indicate the induction of a CD4 T helper cell response. While TT is a potent inducer of CD4 memory T cells in humans (Lundgren, et al. (2003) *Infect Immun.* 71, 1755-1762 and Hengel, et al. (2003) *J. Immunol.* 170, 28-32), this has not been the observation when mice are immunized with free TT. A TT-specific proliferative response from a single dose was observed when lymph node cells were recovered from the mice immunized with the 20:80 TT+bolus treatment (FIG. 7). Consistent with published reports, the in vitro proliferative response was not observed when mice were immunized only with soluble TT unless multiple doses of TT were administered (Lavigne, et al. (2004) *Microbes Infect.* 6, 481-484 and Walker, et al. (1998) *Dev. Biol. Stand.* 92, 259-267). Thus, the ability to detect an antigen-specific proliferative response 28 weeks after a single immunization indicates that immunization with the poly(CPH-SA) 20:80 microspheres generated long-lived memory cells along with plasma cells (antibody secreting B cells) that generally require maturation signals from CD4 helper T cells.

Discussion

Tetanus toxoid (TT) was successfully entrapped in and released from polyanhydride microspheres. The present invention provides a single dose immunogenic composition, such as a vaccine, delivery system based on bioerodible polyanhydride microspheres with the ability to modulate immune response mechanism(s). The polymer itself has a dose-dependent adjuvant effect that can enhance the immune response to an otherwise suboptimal immunogenic dose of TT. The microspheres prolong the release of immunogenic/antigenic TT sufficiently and induce a mature (i.e., secondary) immune response, without requiring additional administrations. The antibody avidity observed when the TT was delivered along with or encapsulated within poly(CPH-SA) 20:80 microspheres is similar to that induced by free TT. However, the antibody avidity is lower when the TT is encapsulated within the more hydrophobic poly(CPH-SA) 50:50 microspheres. The poly(CPH-SA) 50:50 microspheres induces a weak T helper cell response, as suggested by the immune responses that showed no preference for IgG1 or IgG2a production. This could either be due to poor stabilization of the antigen, the slower protein release kinetics, and/or the inhibition of dendritic cell function by this polymer formulation. However, the addition of a bolus of free TT along with the poly(CPH-SA) 50:50 microspheres induces an improved immune response as evidenced by the higher avidity index.

In addition to providing an effective single dose vaccination regimen, the microsphere delivery vehicle offers the opportunity to select the preferred immune response pathway. The preferential reduction of the $T_H2$ immune response and the ability to induce a balanced immune response is a unique and valuable feature of this delivery vehicle that makes it a promising candidate for developing vaccines to intracellular pathogens. Though it is not exactly clear how the APCs process the encapsulated antigen to result in different immune responses, we hypothesize that the immune response may be governed by a combination of the microsphere degradation kinetics, the delay of migration of DCs from the injection site, and by the interaction of the hydrophobic polymer with receptors on the surface of APCs. The implications of these observations may provide the ability to rationally design single dose vaccines employing bioerodible polyanhydride copolymers.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

While the invention is described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

What is claimed is:

1. A composition comprising an amount of an immunogen comprising one or more proteins of a pathogen or an allergen incorporated into bioerodible polyanhydride homopolymer or copolymer microparticles, wherein the amount of the one or more proteins or the allergen is effective to induce a $T_H1$ or a $T_H1$ and a $T_H2$ immune response.

2. The composition of claim 1 wherein the immunogen comprises a bacterial pathogen.

3. The composition of claim 1 wherein the pathogen is a gram-positive bacterium.

4. The composition of claim 1 wherein the pathogen is *C. tetani, C. botulinum, B. anthracis*, or *C. diphtheriae*.

5. The composition of claim 1 wherein the pathogen is a gram-negative bacterium.

6. The composition of claim 1 wherein the pathogen is a virus.

7. The composition of claim 1 wherein the microparticle has a diameter of about 100 nm to about 100 μm.

8. The composition of claim 1 wherein the microparticle has a diameter of about 100 nm to about 75 μm.

9. The composition of claim 1 wherein the microparticles are microspheres of about 100 nm to about 50 μm in diameter.

10. The composition of claim 1 wherein the microparticles comprise a 1,ω-bis(p-carboxyphenoxy)($C_2$-$C_{12}$)alkane.

11. The composition of claim 10 wherein the copolymer is a copolymer of a ($C_4$-$C_8$)alkane with a ($C_5$-$C_{20}$)alkanoic diacid.

12. The composition of claim 11 wherein the ($C_5$-$C_{20}$) alkanoic diacid is sebacic acid (SA).

13. The composition of claim 10 wherein the 1,ω-bis(p-carboxyphenoxy) ($C_1$-$C_6$)alkane is 1,6-(bis-p-carboxyphenoxy)hexane (CPH).

14. The composition of claim 11 wherein the ($C_5$-$C_{20}$) alkanoic diacid is a ($C_8$-$C_{12}$)alkanoic diacid.

15. The composition of claim 10 wherein the immunogen comprises a bacterial pathogen.

16. A method of inducing an immunogenic response in an animal comprising administering to said animal an effective amount of the composition of claim 1.

17. The method of claim 16 wherein the composition is administered in combination with a liquid vehicle.

18. The method of claim 16 wherein the composition is administered by injection.

19. The method of claim 16 wherein multiple microparticle formulations are administered to induce the immunogenic response.

20. The method of claim 16 wherein the administration reduces at least one of the symptoms of infection by the pathogen or of the allergen.

21. The composition of claim 2 wherein the immunogen comprises a lysate of the bacterial pathogen.

22. The composition of claim 15 wherein the immunogen comprises a lysate of the bacterial pathogen.

23. The composition of claim 1 further comprising an amount of an immunogen of the pathogen or the allergen which is not incorporated into the microparticles.

24. A composition comprising bioerodible polyanhydride copolymer microparticles comprising a 1,ω-bis(p-carboxyphenoxy)($C_2$-$C_{12}$)alkane prepared by combining an aqueous solution comprising an amount of an immunogen comprising one or more proteins of a pathogen or an allergen and a non aqueous solution comprising copolymers comprising a 1,ω-bis(p-carboxyphenoxy)($C_2$-$C_{12}$)alkane so as to form an emulsified mixture, adding a solvent so as to form a double emulsion having bioerodible polyanhydride copolymer microparticles comprising a 1,ω-bis(p-carboxyphenoxy)($C_2$-$C_{12}$)alkane and the immunogen, and purifying from the double emulsion the bioerodible polyanhydride copolymer microparticles comprising a 1,ω-bis(p-carboxyphenoxy)($C_2$-$C_{12}$)alkane and the immunogen.

25. The composition of claim 24 wherein the polyanhydride is a copolymer with a ($C_5$-$C_{20}$)alkanoic diacid.

26. The composition of claim 25 wherein the ($C_5$-$C_{20}$) alkanoic diacid is sebacic acid.

27. The composition of claim 25 wherein the ratio of the 1,ω-bis(p-carboxyphenoxy)($C_2$-$C_{12}$)alkane to the ($C_5$-$C_{20}$) alkanoic diacid is about 20:80.

28. The composition of claim 24 wherein the ratio of the 1,ω-bis(p-carboxyphenoxy)($C_2$-$C_{12}$)alkane in the copolymer is about 20:80.

29. The composition of claim 24 wherein the ratio of the 1,ω-bis(p-carboxyphenoxy)($C_2$-$C_{12}$)alkane in the copolymer is about 50:50.

30. The composition of claim 23 wherein the immunogen that is not incorporated into the microparticles is different than the immunogen incorporated into the microparticles.

* * * * *